United States Patent [19]

Kriesel et al.

[11] Patent Number: 5,330,426
[45] Date of Patent: Jul. 19, 1994

[54] MIXING AND DELIVERY SYRINGE ASSEMBLY

[75] Inventors: Marshall S. Kriesel, Saint Paul; Thomas N. Thompson, Richfield, both of Minn.

[73] Assignee: Science Incorporated, Bloomington, Minn.

[21] Appl. No.: 930,749

[22] Filed: Aug. 13, 1992

[51] Int. Cl.$^5$ .............................................. A61M 37/00
[52] U.S. Cl. ........................................ 604/89; 604/82; 604/87
[58] Field of Search ................................. 604/82–93, 604/148, 139, 890.1, 200–205, 226, 411–416, 221–222, 231–232, 235, 244–246

[56] References Cited

U.S. PATENT DOCUMENTS

| | | | |
|---|---|---|---|
| 3,080,866 | 3/1963 | Friedman | 604/88 |
| 3,552,387 | 1/1971 | Stevens | 604/88 |
| 3,563,373 | 2/1971 | Paulson | 206/63.2 |
| 3,724,460 | 4/1973 | Gomez et al. | 604/88 |
| 3,766,919 | 10/1973 | Cloyd . | |
| 3,995,630 | 12/1976 | van de Veerdonk . | |
| 4,479,796 | 10/1984 | Kallok | 604/93 |
| 4,601,893 | 7/1986 | Cardinal | 424/15 |
| 4,713,062 | 12/1987 | Stevanato | 604/203 |
| 4,857,053 | 8/1989 | Dalton | 604/93 |
| 4,861,335 | 8/1989 | Reynolds | 604/88 |
| 5,067,948 | 11/1991 | Haber et al. . | |
| 5,112,307 | 5/1992 | Haber et al. . | |
| 5,112,317 | 5/1992 | Michel . | |
| 5,114,406 | 5/1992 | Gabriel et al. . | |
| 5,122,117 | 6/1992 | Haber et al. . | |
| 5,137,511 | 8/1992 | Reynolds | 604/88 |
| 5,158,546 | 10/1992 | Haber et al. | 604/87 |

FOREIGN PATENT DOCUMENTS

| | | |
|---|---|---|
| WO92/10225 | 6/1972 | PCT Int'l Appl. . |
| WO86/06618 | 11/1986 | PCT Int'l Appl. . |
| WO91/10417 | 7/1991 | PCT Int'l Appl. . |
| 1313339 | 4/1973 | United Kingdom . |
| 1413734 | 11/1975 | United Kingdom . |

OTHER PUBLICATIONS

Dorland's Illustrated Medical Dictionary, 24th edition, W. B. Saunders Company, p. 1460 (1965).

*Primary Examiner*—C. Fred Rosenbaum
*Assistant Examiner*—Vanitha Alexander
*Attorney, Agent, or Firm*—J. E. Brunton

[57] ABSTRACT

A device for intermixing a first component, such as a parenteral fluid with a second component, such as an immobilized drug carried by a scaffold to form a beneficial agent which, following the mixing step, can be dispensed directly from the device for infusion into a patient. The device includes novel mechanisms for mateably interconnecting a container, such as a glass vial containing the first component with a housing having a fluid outlet which houses a sealed container containing the second component, and then for controllably mixing the components under sterile conditions to form an injectable solution which is automatically dispensed through the fluid outlet of the device.

23 Claims, 3 Drawing Sheets

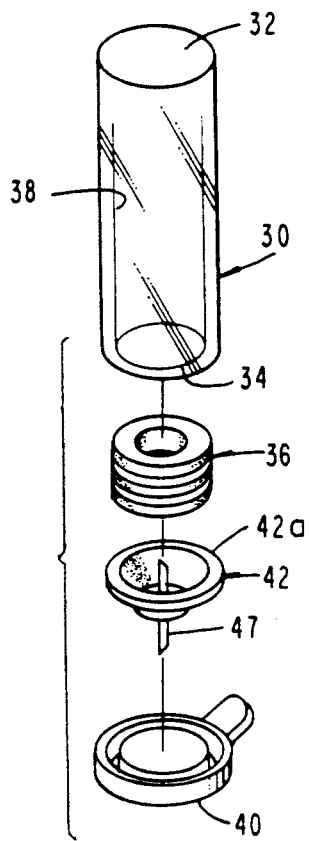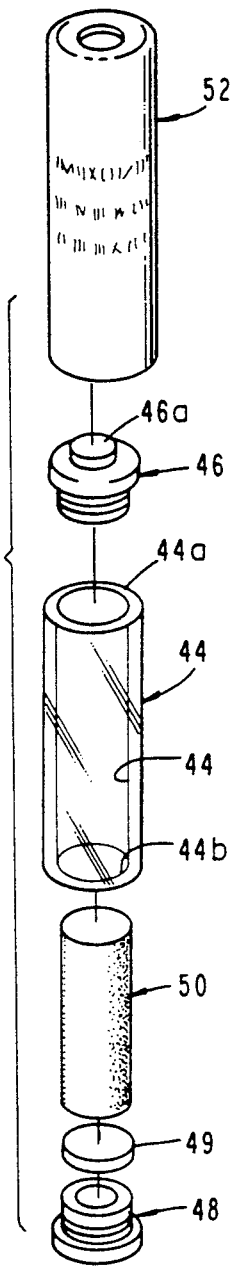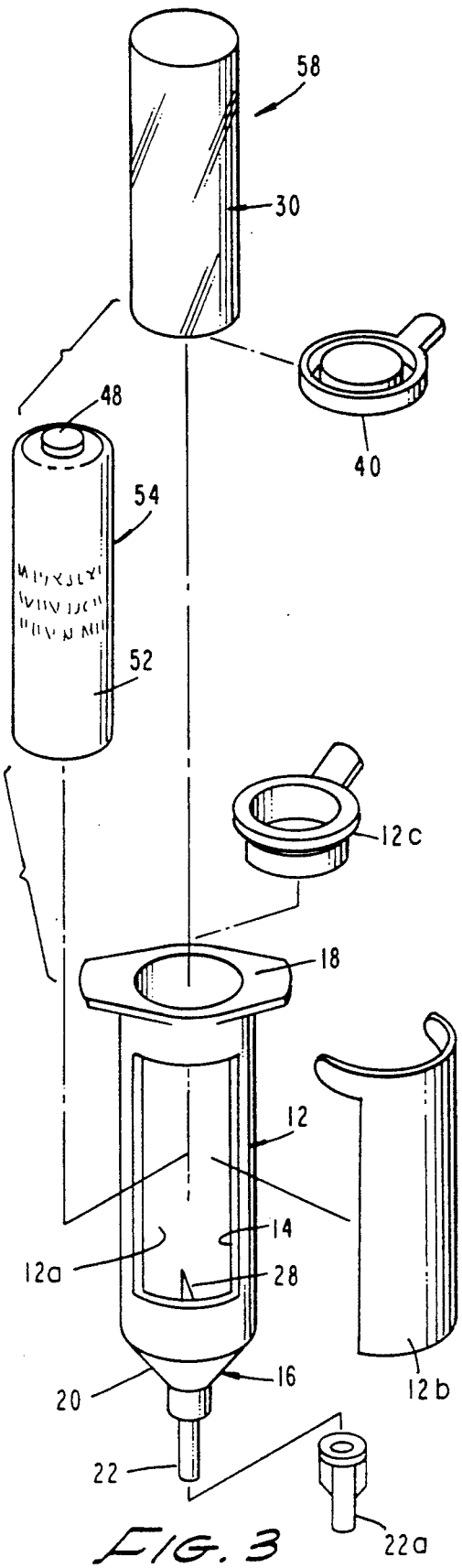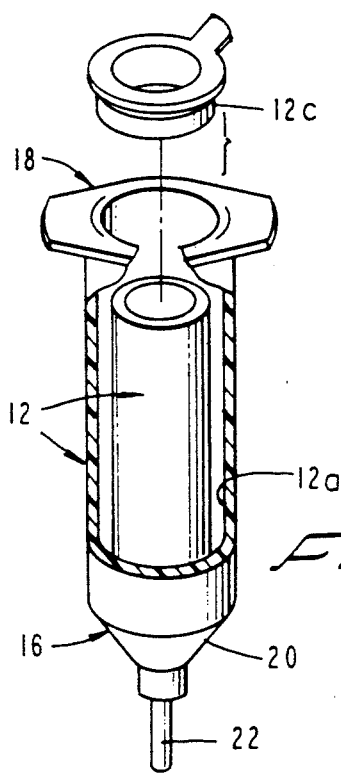

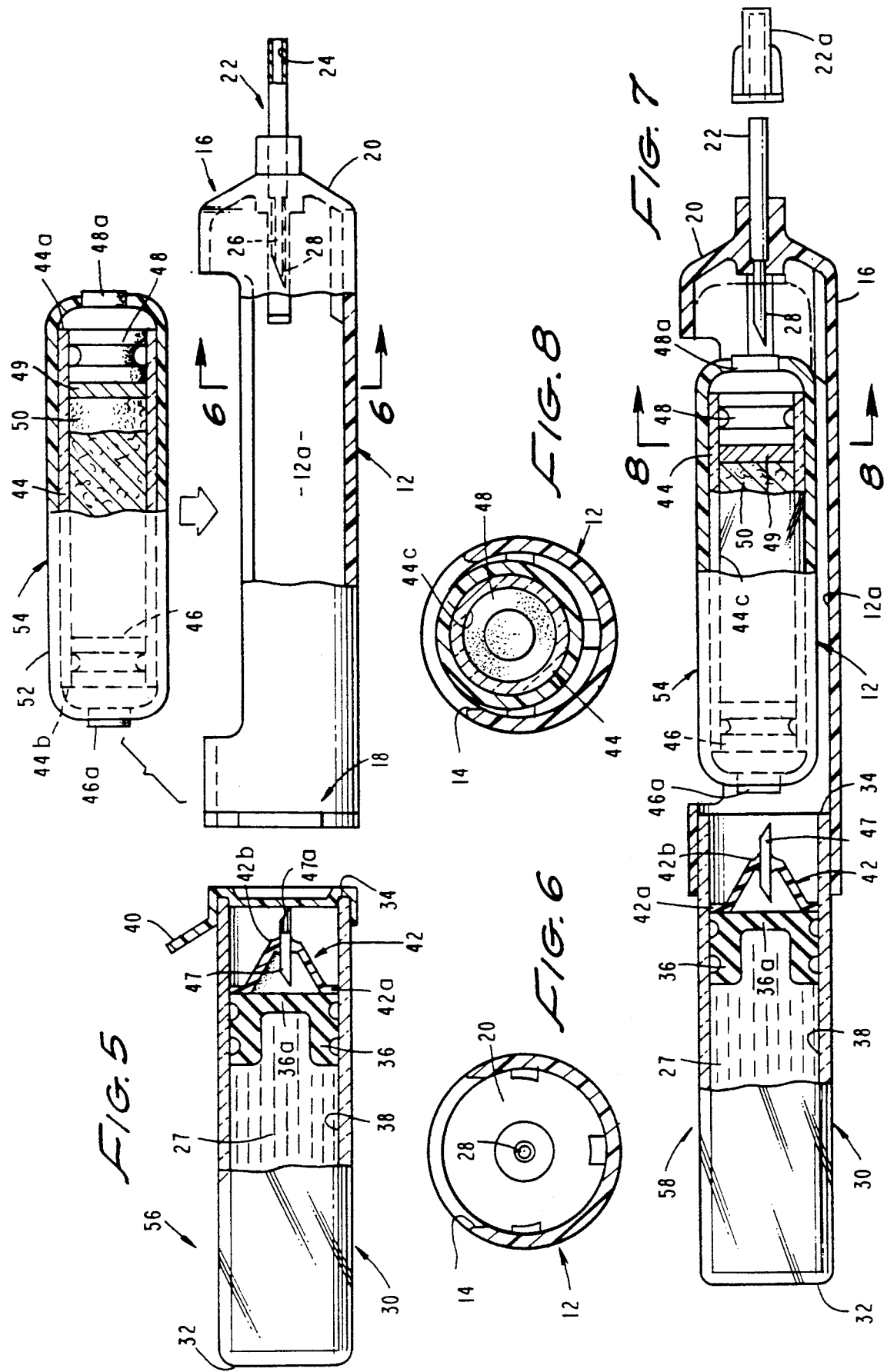

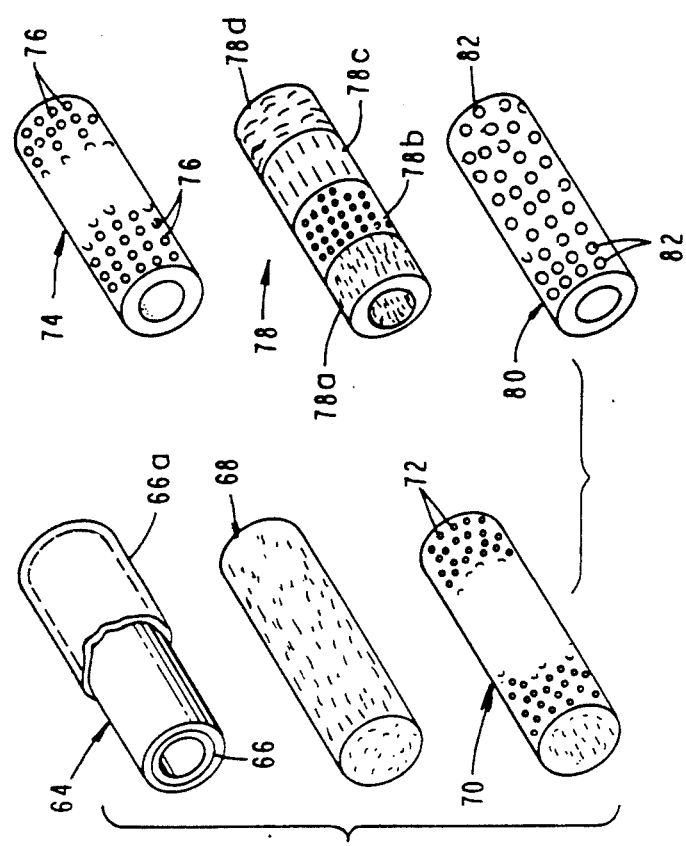
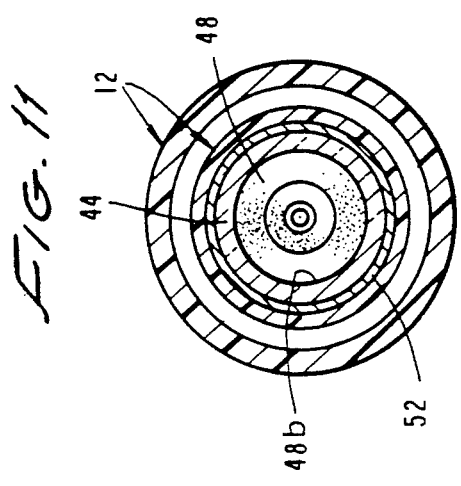
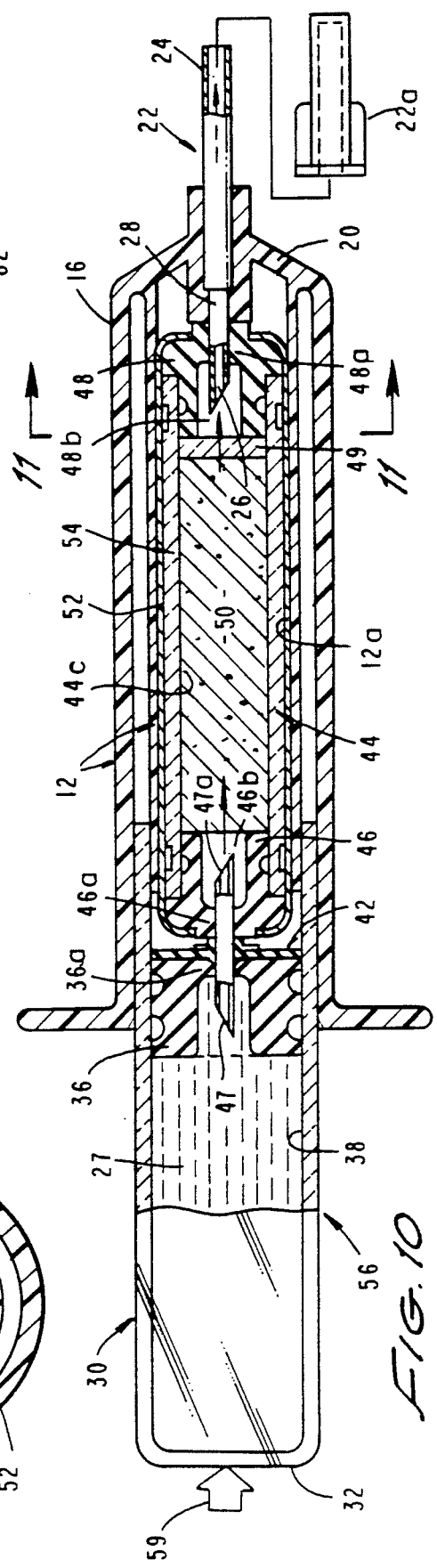

MIXING AND DELIVERY SYRINGE ASSEMBLY

BACKGROUND OF THE INVENTION

1. Field of the Invention

The present invention relates generally to syringes of the character used to administer drugs by injecting them into subcutaneous tissue. More particularly, the invention concerns a syringe of novel design in which a first component, such as a sterilized diluent, can be intermixed with a second component, such as a drug to form a beneficial agent which can be dispensed directly from the syringe.

2. Discussion of the Invention

Hypodermic syringes are commonly used for injecting into a patient beneficial agents, such as drugs in liquid form. Typically, the beneficial agent to be injected is typically drawn into the syringe from another container, such as a glass vial, bottle or the like having a pierceable, self-sealing stopper. When the beneficial agent, such as a pharmaceutical, is in powder form prior to injection, it must be mixed with a carrier liquid or diluent, such as saline solution, dextrose solution and sterilized water.

Mixing of powdered pharmaceuticals with the carrier liquid has been accomplished in several ways, many of them being quite crude. For example, a common practice is to inject a small quantity of the liquid carrier into the vial to dissolve the powdered component. Then, using a cannula and syringe, the solution thus formed is injected into a larger container containing the liquid carrier. This method is quite tedious and provides substantial opportunities for contamination and error.

Because infusion of medicaments is most often accomplished in a hospital environment, it is the nurse, doctor or medical technician who mixes the drug and diluent, usually at a time
before administration of the drug to the patient. This mixing step can be time consuming and hazardous, as for example, when toxic drugs are involved. Further, since many of the prior art mixing devices are crude and imprecise, accurate, sterile and thorough mixing of the drug and the diluent is most difficult and time consuming. Accordingly, such devices are not well suited for use in the home environment.

In the past several attempts have been made to provide a syringe apparatus in which separate components can be intermixed prior to patient injection. Exemplary of such prior art devices are those disclosed in U.S. Pat. No. 2,724,383 issued to Lockhart; in U.S. Pat. No. 3,336,924 issued to Sarnoff, et al and U.S. Pat. No. 3,477,432 issued to Shaw. The Lockhart apparatus includes segregating compartments in the form of connecting, interfitting containers with associated cannula means which are manipulatable simultaneously so as to provide intercommunication between the compartments via the cannula means. the components to be mixed are stored in the interfitting containers and then are intermixed by suitably manipulating the containers. The device can be brought into "administering" condition by withdrawal of one of the empty containers to produce a hypodermic syringe type structure.

Sarnoff, et al. discloses several types of syringe packages, each comprising a vial containing a medicament, a stopper closing the vial, a connector member attached to the vial and extending beyond the stopper, and a syringe interconnected to the connector member. In one form of the Sarnoff invention, the needle of the syringes is partially embedded in the stopper. In another form of the invention, a double needle unit is carried within the connector member so that one needle can penetrate the stopper on the vial and the other can penetrate a stopper on a second container. In this last described embodiment, the double needle unit provides the flow path between the vial and the second container so that component mixing can occur.

In the Shaw patent various versions of combined mixing and injecting syringes are disclosed. The Shaw device enables intermixing of two ingredients which may be powders or liquids and provides for the injection of the mixture after the mixing step has been accomplished.

The apparatus of the present invention provides a totally new and novel approach to precisely intermixing two components and then expelling the mixture from the device through a needle or blunt cannula. More particularly, the apparatus comprises a housing within which an immobilized drug cartridge containing a selected drug or other beneficial agent can be inserted. One end of the housing is open and the opposite end is provided with an inwardly extending needle and an outwardly extending blunt end cannula. A diluent assembly including a sealed vial is then inserted into the open end of the housing and urged telescopically inward of the housing. This causes a double ended needle to simultaneously pierce the sealed vial and a rear seal provided on the drug cartridge thereby placing the vial and the drug cartridge in fluid communication. A continued inward force on the diluent assembly will cause the inwardly extending needle of the housing to pierce the forward seal of the drug cartridge, placing the interior of the drug cartridge in fluid communication with the blunt end cannula. As the diluent flows through the drug cartridge, it will controllably intermix with the immobilized drug forming an injectable solution which can be expelled from the device via the blunt end cannula.

SUMMARY OF THE INVENTION

It is an object of the present invention to provide a device for precisely intermixing a first component, such as a parenteral liquid, with a second component, such as a pharmaceutical, to form an injectable solution which can be dispensed from the device following mixing.

It is another object of the invention to provide a device of the aforementioned character in which the first and second components can be separately stored in sealed containers until they are coupled with the dispensing portion of the device for mixing and subsequent dispensing.

Another object of the invention is to provide a device as described in the preceding paragraphs in which the second component which can be any type of beneficial agent such as a drug, a pharmaceutical or a biological agent is removably affixed to a scaffold such as a rigid substrate which can be safely and conveniently stored within a sealed container until it is to be mixed with the second component.

It is an object of the present invention to provide an apparatus of the character described in the preceding paragraph which provides the opportunity to add in a sterile environment to a diluent or other parenteral fluid contained within a glass vial, selected elements, chemical compounds and biologically active materials, including drugs, medicaments, biological agents, and other therapeutic agents (additives). This addition is accomplished by removably affixing the selected additives to various forms of support structures or scaffolds which can be placed within a sealed container which can, in turn, be placed in fluid communication with the glass vial. In this way, the diluent within the glass vial can expeditiously be rendered therapeutically active upon reacting and releasing of the additive carried by the substrate into the diluent.

Another object of the invention is to provide an apparatus of the character described in which the adding means, including the scaffold which carries the second component, or additive, is maintained within a completely sterile environment within the sealed container until immediately prior to the releasing and controlled mixing of the additive and the diluent.

Another object of the invention is to provide an apparatus of the class described in which a wide variety of selected additives can be removably affixed to the scaffold or substrate that is stored within the sealed container for controlled intermixing with the liquid contained within the glass vial.

Another object of the invention is to provide a device of the aforementioned type in which toxic or other hazardous compounds, including those with short therapeutic lives can be separately and safely stored until immediately prior to their use following being intermixed with the liquid compound contained within the diluent glass vial.

Another object of the invention is to provide a device of the character described in the preceding paragraph in which toxic or other hazardous compounds which are to be intermixed with the liquid component can be separately and safely handled during the manufacture of the substrate portion of the device and in which the substrate carrying the hazardous materials can, following manufacture, be safely stored within the sealed container until time of use.

Another object of the invention is to provide a device of the class described in which the additive or beneficial agent components, such as a drug or pharmaceutical, can be uniformly deposited or otherwise removably affixed to the scaffold or additive support in a manner to maximize easy releasibility and separation of the additive and complete intermixing thereof with the liquid component.

Another object of the invention is to provide a mixing and dispensing device which is of simple construction and is easy and safe to use by relatively unskilled technicians.

Another object of the invention is to provide a device of the aforementioned character in which precise mixing of the first and second components is automatically accomplished by the telescopic movement of a sealed vial containing the first diluent component into a hollow housing which supports the sealed container housing the scaffold upon which the second component is immobilized.

Another object of the invention is to provide a device as described in the preceding paragraph in which the mixed solution is automatically and controllably dispensed from the device as a result of the telescopic movement of the sealed container into the hollow syringe housing.

Still another object of the invention is to provide a device of the class described which embodies a minimum number of moving parts and one which can be inexpensively manufactured in quantity so that it can be economically disposed of after use.

BRIEF DESCRIPTION OF THE DRAWINGS

FIG. 1 is a generally perspective, exploded view of one form of the mixing and dispensing device of the present invention.

FIG. 2 is an enlarged, generally perspective, exploded view of a sealed container which contains the second component such as a drug or other beneficial agent which is to be intermixed with the first component such as a diluent which is contained in the first container shown in the upper portion of FIG. 1.

FIG. 3 is a generally perspective, exploded view illustrating the manner in which the first and second containers of the device are mated with the hollow housing portion of the device used to dispense the intermixed solution.

FIG. 4 is a generally perspective view of the dispensing housing portion of the device showing the second container containing the beneficial agent disposed within an internal chamber of the dispensing housing.

FIG. 5 is an enlarged, side-elevational view of one form of the device of the present invention partly broken away to show internal construction.

FIG. 6 is a cross-sectional view taken along lines 6—6 of FIG. 5.

FIG. 7 is a side-elevational view partly in cross-section similar to FIG. 5 but showing the first and second component containers of the invention mated with the dispensing housing portion of the device.

FIG. 8 is cross-sectional view taken along lines 8—8 of FIG. 7.

FIG. 9 is a generally perspective view of various forms of the supporting substrate or additive scaffold of the invention upon which the second component is removably affixed.

FIG. 10 is an enlarged side-elevational view partly in cross-section similar to FIG. 7 but showing the position of the component parts after the first container has been telescopically moved inwardly of the dispensing housing.

FIG. 11 is a cross-sectional view taken along lines 11—11 of FIG. 10.

DESCRIPTION OF THE INVENTION

In the paragraphs which follow, wherein the device of the invention will be discussed, the following terms will have the following meanings:

Element—any of the fundamental substances that consist of atoms of only one kind and that singly or in combination constitute all matter.

Additive—the element, compound, substance, agent, biologically active material, pharmaceutically active material or other material which is to be added to the fluid contained in the container means of the device of the invention.

Parenteral Fluid—any solution which may be delivered to a patient other than by way of the intestines, including water, saline solutions, alkalizing solutions, dextrose solutions, acidifying solutions, electrolyte solutions, reagents, solvents and like aqueous solutions.

Beneficial Agents—any drug, medicament, pharmaceutical, medical polymer, enzyme, element, chemical compound or other material useful in the diagnosis, cure, mitigation, treatment or prevention of disease and for the maintenance of the good health of the patient.

Biologically Active Material—a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such biochemical compounds biologically functioning as antibodies, antigenic substances, enzymes, co-factors, inhibitors, lectins, hormones, hormone producing cells, receptors, coagulation factors, anti-fungal agents, growth enhancers, histones, peptides, vitamins, drug, cell surface markers and toxins, among others known to those skilled in the art. Of the group of biologically active materials described, proteins are of utmost current interest because of the large molecule genetically engineered bio-pharmaceuticals as those species to be immobilized on the additive carriers hereinafter to be described. A discussion of the use of biomosic polymers as carriers for biologically active materials is set forth in European Patent Application 0,430,517 A2.

Adding Means—an additive and any means for presenting the additive to the fluid flowing through the fluid passageways of the fluid delivery device of the invention in a manner such that all or any part of the additive will be added to the fluid. The adding means comprises the additive and the additive presentation means which may take the form of a scaffold, a functional support, or carrier, an anchorage, a deposition site or element holder, with or without some type of intermediate matrix such as an azlactone functional material to provide a reactive intermediate support as described in EPO Application 0 392 735 AZ and in EPO Application WO 88/0706 2.

Additive Presentation Means—any means such as a scaffold, functional support or substrate for presenting the additive to the fluid flowing through the device. The scaffold or functional substrate can comprise a polymer, copolymer, and inter-polymer, a ceramic, a crystal sponge, a carbon based matrix, a celullosic, glass, plastic biomosaic polymers, azlactone-functional materials such as coatings, polymer beads, adduct beads, carboxylate-functional polymer beads, gums, gels, filaments and like carriers.

The adding means of the invention can take several different forms such as those illustrated in FIG. 9. However, in its preferred form, the adding means comprises a microstructure with interconnecting voids such as a cylindrically shaped, microporous, polymeric functional support structure 50 (FIG. 2) to which various additives, including beneficial agents such as drugs, biologically active materials, and various chemical elements and compounds can be releasably connected. These additives are carried by the structure and extend into the voids in a manner such that, as the liquid within the second container, such as a diluent, reagent or other aqueous solvent flows around and about the support assembly, in the manner presently to be described, the additives will be presented to the liquid flow and efficiently added to the liquid.

The additives themselves can also take various physical forms including liquid, solid, granular, powder, particle, gel, wax hydrocolloid carriers, such a gum film, tablet, crystalline, emulsions, microcrystalline, microcapsules, microspherical, spray dried compounds and lypohilized compounds and saturants. The additives can be removably connected to, immobilized on, impregnated within or supported by support means in a number of ways. The additives can be chemically or mechanically attached, affixed, or bound directly or indirectly through cooperation with an intermediate matrix. They can be captured, affixed, linked, or cross-linked, anchored to the surfaces of the support, or surface active agent, or they can be absorbed, reaction catalyzed, electrostatically encapsulated, attached by chemical modification in to the carrier surface, polymerized on or through the carrier, localized, entrapped, deposited, suspended or occluded within voids, cells, tubules and interstices formed in the support. One important method for removably affixing the additive to the functional support means includes treating the functional support means with a compound having reactive functional groups such as azlactone functional compounds with their high binding capacity. In certain applications, the biologically active material can be bound at the surfaces of biomosaic polymers in the manner described in EPO Patent No. 0 430 517 A2. Similarly, graft copolymers can be used in the manner described in U.S. Pat. No. 5,013,795 issued to Coleman, et al. In this way complexing agents, catalysts and biological materials such as enzymes or other proteins as well as biomacromolecules can be attached to the carrier.

Similarly, the additives can be immediately separated from the functional support and added to or intermixed with the liquid flowing through the device by one or more of various mechanisms, including chemical reaction, dissolution, debinding, delinking bioseparation, diffusion, washing, disintegration, erosion, disassociation, desorbsion, solubilization, leething, enzymatic cleavage, biological reaction, osmosis, separated from ring opening materials and like separation means.

Description of the Invention

Referring to the drawings and particularly to FIGS. 1, 2, 3 and 4, the device of the present invention for intermixing a first fluid component with a second component and then for dispensing the mixture therefrom is shown in an exploded form in FIG. 3. The device of the embodiment of the invention there shown comprises a hollow housing 12 having a longitudinally extending opening 14 in the wall thereof and first and second ends 16 and 18. Opening 14 is initially closed by a pealably removable, sterile barrier patch 12b. As best seen by referring to FIG. 3, the second end 18 of housing 12 is temporarily closed by a removable cap 12c, while the first end 16 is closed by a closure wall 20. Connected to closure wall 20 and extending outwardly from housing 12 is a blunt end cannula 22 which forms the fluid outlet of the housing 12. Cannula 22 has an internal flow passageway 24 which is in communication with a fluid flow passageway 26 provided in an inwardly extending cannula 28 which is also connected to end closure wall 20. Passageway 24 is temporarily closed by a cannula cap 22a.

Container means which can be removably interconnected with housing 12 is provided to contain a first fluid component such as a diluent or other parenternal fluid 27 (FIG. 5). This container means is most clearly illustrated in FIG. 1 and comprises a glass vial 30 having a closed end 32 and an open end 34. Open end 34 of vial 30 can be closed by a penetrable plug 36 which can be constructed of any suitable needle puncturable elastomeric material such as soft rubber. In a manner presently to be described, plug 36 is telescopically movable within an internal chamber 38 of glass vial 30. For purposes of sterile presentation, a tear-away cap 40 is provided to overlay both plug 36 and open end 34 of vial 30. Disposed intermediate cap 40 and plug 36 is flow means for permitting the fluid contained within the glass vial to flow outwardly thereof after cap 40 has been removed from the vial assembly. Flow means is here provided in the form of a generally frustro-conically shaped, collapsible wall element 42. As best seen by referring to FIG. 5, element 42 includes a circular base flange portion 42a which is adapted to engage the outer surface of plug 36 and a circular end wall 42b through which a double ended cannula or needle 47 extends. Needle 47 includes a fluid passageway 47a which, in a manner presently to be described, permits fluid contained within glass vial 30 to flow outwardly of the vial interior toward housing 12 following mating of the first container means with the dispensing housing 12.

Forming an extremely important aspect of the device of the present invention is adding means for adding a second component such as a drug or other beneficial agent to the first fluid component contained within vial 30. In the form of the invention shown in the drawings, the adding means comprises an assembly of the character best illustrated in FIG. 2. More particularly, the adding means here comprises a cartridge 44 having first and second open ends 44a and 44b. Open end 44a is sealed by a first sealing means while open end 44b is sealed by a second sealing means. The first and second sealing means are here shown as penetrable seals 46 and 48 respectively which are sealably received within the open ends of cartridge 44. Seals 46 and 48 can be constructed of any suitable non-coring needle puncturable elastomeric material such as a soft rubber or silicone.

Disposed internally of cartridge 44 is the additive carrying means of the invention here shown as a cylindrically shaped porous substrate or scaffold 50. Substrate 50 is preferably a microporous, polymeric functional support to which various additives including beneficial agents such as drugs, biologically active materials, and chemical elements and compounds can be releasably connected. These additives are supported by the scaffold or substrate 50 in a manner such that as the liquid component contained within the glass vial, such as a diluent, reagent, or aqueous solvent flows around, about and through the scaffold, the additives will be reacted, released, separated and intermixed with the liquid component. In a manner presently to be described, the additives are uniquely presented to the fluid flow so that they can be efficiently added to the first liquid component contained within the glass vial. Surrounding cartridge 44, which may also be constructed of glass, plastic or other suitable material is a shrink-wrap label or polyolefin overwrap 52 having indicia imprinted thereon identifying the additive or beneficial agent that is immobilized on the scaffold 50. Overwrap 52 also functions to retain pierceable plugs 46 and 48 in place within vial 44.

Turning now to FIGS. 3, 5, and 7, the adding means, which is generally identified in FIG. 3 by the numeral 54, is receivable within the interior chamber 12a of the dispensing housing 12 through the opening 14 provided in the wall thereof. As indicated in FIG. 3, following removal of the sterile barrier patch 12b which sealably covers opening 14, the assemblage 54 can be installed through the opening 14 so that it securely nests within internal chamber 12a in the manner shown in FIG. 7.

Assemblage 54 can be of a polarized configuration well known in the art, such as by an indexed spacer, so that the assemblage can be received with chamber 12a in only one orientation. The first container means which is generally identified in FIG. 5 by the numeral 56 is adapted to be mated with housing 12 in a manner now to be described. The first step in the mating process comprising the step of removing barrier cap 40 so as to form the subassemblage identified in FIGS. 3 and 7 by the numeral 58. After barrier cap 12c is removed, the plugged end of assemblage 58 is then telescopically inserted into the open end 18 of housing 12 in the manner shown in FIG. 7 so as to maintain a sterile fluid path. Inward pressure directed against subassembly 58 in the direction of the arrow 59 in FIG. 10 will cause several events to occur simultaneously. One such event, as illustrated in FIG. 10, comprises the collapsing of wall 42 of the flow means in a manner such that double ended needle 47 will simultaneously pierce portion 36a of penetrable plug 36 of the container means and piercable portion 46a of sealable plug 46 of the adding means. This places the interior of glass vial 30 in fluid communication with the internal chamber of cartridge 44 so that fluid contained within the glass vial can flow inwardly into the inner chamber 44c of cartridge 44 and then around, about and through substrate 50. The exertion of a continued inward pressure against the glass vial in the direction of arrow 59 will cause needle 28 of housing assembly 12 to penetrate portion 48a of plug 48 of the adding means thereby permitting fluid flow between the adding means and the outlet or cannula 22 of the dispensing subassembly or syringe housing 12. This combination of needle 28 and cannula 22 comprises a second flow means of the invention for permitting fluid flow between the adding means and the outlet of dispensing housing 12.

As an inward pressure on the glass vial is maintained, penetrable plug 36 will travel longitudinally relative to the glass vial inwardly thereof. This will cause the liquid contained within the glass vial to flow rapidly through the passageway 47a in double-ended needle 47 and into the internal chamber 44c of cartridge 44. Fluid flowing through piercable plug 46 will be distributed in a uniform outwardly direction via portion 46b of the plug and the proximal interface of porous support 50. As the fluid passes through the internal chamber of the cartridge, it will flow around, about and through substrate 50 in a manner to cause the additive immobilized thereon or otherwise removably affixed thereto to separate and thoroughly intermix with the liquid to form an injectable solution. The pressure of the fluid flowing through the adding means will also cause controllable ejection of the injectable solution through passageway 24 of cannula 22. Portion 48b of plug 48 functions as a fluid collection means from a filter 49 and the distal interface well of substrate 50 to focus fluid flow toward passageway 26 of cannula 28. Filter 49, which may be a polyethelene, hydrophilic depth filter with a screen base, is interposed between scaffold 50 and plug 48. Filter 49 sealably engages the inner wall of glass ampule 44 and functions to trap particulate or gaseous matter which may be contained in the mixed solution. This particulate filter and gas containment means can be configured as desired for the particular application at hand.

Turning now to FIG. 9 various other forms of adding means or additive assemblies are there illustrated. For example, numeral 64 identifies an assembly comprising a plurality of layers 66 each of which is coated with the selected additive. In some instances a microporous membrane film or skin 66a envelops the assembly to permit contaminate free handling. The layers 66 are overlayed in the manner shown in the drawing to provide a multiplicity of exposed surfaces and alternatively spaced reaction sites which are exposed to the diluent as it flows through chamber 44c.

Numeral 68 designates a porous substrate with open interstitial cells or pores and interconnecting voids, such as a porous ceramic with various coatings containing one or more additives deposited within the voids. The selected additives such as elements, chemical compounds or drugs are contained within the deposited material and are deposited, or immobilized thereon with or without the use of an intermediate matrix by techniques well known to those skilled in the art. The additives contained within the voids are, of course, presented or exposed to the diluent, are separated from the scaffold and then are introduced into the sterile diluent or other liquid as it flows through chamber 44c.

Another form of additive assembly designated in FIG. 9 by the numeral 70 comprises a generally tubular member having a multiplicity of alternate sized pores 72 which are plugged with selected additives such as chemical compounds and beneficial agents, or medicaments.

Still another form of the additive assembly is identified in FIG. 9 by the numeral 74. This assembly comprises a cylindrical, porous plug-like member made up of a multiplicity of fused together microspheres 76 each of which is coated with a separation or reactive coating acting as useful reactive or adduct supports for the affinity attachment and subsequent release of an additive such as a biologically active material or other beneficial agents.

Another slightly more complex additive assembly is identified by the numeral 78. This assembly is made up of a plurality of spaced-apart, porous disk shaped wafers 78a, 78b, 78c and 78d each wafer being of the same or different construction and porosity and each having a multiplicity of reactive sites presenting to the liquid flow specially selected individual species of additives such as beneficial agents, elements or compounds so that multiple reactivities and selectivities and mixing can be achieved. With this construction, a wide variety of liquid flow rates, and complex sequential separations and priority staged substance introduction into the outlet cannula can be achieved by specially designing each of the wafers having unique affinity and separation characteristics that cooperate to make up the functional structural support.

The numeral 80 of FIG. 9 identifies yet another form of the additive means of the invention. In this form of the invention, a generally cylindrically shaped insoluable functional support means is formed from a biomosaic polymer 82 which may be porous or non-porous presenting a multiplicity of reactive sites for bioseparation of materials bound at the surfaces of the polymer.

Assemblies 64 through 80 which may be soluble or insoluble are intended to merely exemplify, not to limit, the wide variety of materials, constructions and techniques for drug compound or agent affinity and separation that can be used to introduce the desired additives into the liquid flow introduced into the internal chamber 44c of the adding means. Similarly vials 30 and 44 can be constructed of various materials other than glass such as plastic. In like manner housing 12 can be constructed from various materials including polyethylene, polyesters, polyamides, polycarbonates and the like.

After the diluent or other parenteral fluid is introduced into chamber 44c and mixed with the additive, the solution is dispensed from the device via cannula 22 to the environment of use.

Having now described the invention in detail in accordance with the requirements of the patent statutes, those skilled in this art will have no difficulty in making changes and modifications in the individual parts of their relative assembly in order to meet specific requirements or conditions. Such changes and modifications may be made without departing from the scope and spirit of the invention, as set forth in the following claims.

We claim

1. A device for intermixing a first fluid component with a second component and for dispensing the mixture from the device comprising:
   (a) a housing having an internal chamber with an outlet;
   (b) container means connected to said housing for containing the first fluid component, said container means being movable relative to said chamber from a first position to a second position;
   (c) adding means disposed within said internal chamber for adding said second component to said first fluid component upon movement of said container means toward said second position to form in infusible mixture, said adding means comprising a scaffold upon which said second component is removably carried; and
   (d) flow means for permitting fluid flow between said adding means and said outlet upon movement of said container means toward said second position, whereby said infusible mixture will be dispensed through said outlet as a result of movement of said container means toward said second position.

2. A device as defined in claim 1 in which said adding means further comprises a container having an internal chamber for containing said scaffold.

3. A device as defined in claim 2 in which said scaffold comprises a microporous member having a microstructure of interconnecting voids, said second component extending into said voids.

4. A device as defined in claim 3 in which said first fluid component comprises a parenteral liquid.

5. A device as defined in claim 4 in which said second component comprises a beneficial agent.

6. A device as defined in claim 4 in which said second component comprises a pharmaceutical.

7. A device as defined in claim 4 in which said second component comprises a drug.

8. A device for intermixing a first liquid component with a second component to form an infusible solution and for dispensing the fusible solution from the device into the environment of use, said device comprising:
   (a) a hollow housing having an internal chamber and first and second ends;
   (b) a cannula connected to said second end of said hollow housing;
   (c) container means connected to said first end of said hollow housing for telescopic movement within said internal chamber from a first position to a second position;
   (d) adding means removably receivable within said internal chamber for adding said second component to said first liquid component upon movement of said container means toward said second position, said adding means comprising a scaffold upon which said second component is immobilized; and (e) first flow means for establishing liquid flow between said adding means and said cannula upon movement of said container means toward said second position whereby said infusible solution will be dispensed from the device through said outlet as a result of movement of said container means toward said second position.

9. A device as defined in claim 8 in which said adding means comprises a container for containing said substrate, said container having a first end sealed by a first sealing means and a second end sealed by a second sealing means.

10. A device as defined in claim 9 in which said container means comprises a glass vial having a chamber for containing the first fluid component, said chamber of said glass vial being sealed by a penetrable plug.

11. A device as defined in claim 10 further including second flow means for establishing liquid flow between said chamber of said glass vial and said container containing said substrate upon movement of said container means toward said second position.

12. A device as defined in claim 11 in which said second flow means comprises a double ended needle for simultaneously penetrating said penetrable plug and said first sealing means of said container containing said substrate upon movement of said container means toward said second position.

13. A device as defined in claim 12 in which said first flow means comprises a needle having a central bore in communication with said cannula, said needle being so constructed and arranged as to pierce said second sealing means of said container containing said substrate upon movement of said container means toward said second position.

14. A device as defined in claim 13 in which said second component comprises a beneficial agent.

15. A device as defined in claim 13 in which said second component comprises a drug.

16. A device as defined in claim 13 in which said scaffold comprises a porous cylinder, said second component being immobilized within the pores thereof.

17. A device as defined in claim 13 in which said scaffold comprises a biomosaic polymer.

18. A device as defined in claim 13 in which said scaffold comprises an adduct support.

19. A device as defined in claim 13 in which said housing is provided with a longitudinally extending opening for receiving said adding means.

20. A mixing and infusion device comprising:

(a) a hollow housing having a longitudinally extending opening and first and second ends, said second end being open;

(b) an outwardly extending cannula connected proximate said first end of said housing;

(c) an inwardly extending cannula connected proximate said first end of said housing and being in fluid communication with said outwardly extending cannula;

(d) a sealed cartridge receivable within said longitudinally extending opening in said hollow housing, said cartridge containing adding means including a substrate for removably carrying a beneficial agent and having first and second ends, said first end being sealed by a first penetrable seal and said second end being sealed by a second penetrable seal; and (e) a sealed fluid container telescopically receivable within said second open end of said housing for movement between first and second positions, said fluid container containing a liquid component and having:

(i) a closed first end;
(ii) an open second end;
(iii) a penetrable plug sealably disposed within said open second end for movement relative to said fluid container; and
(iv) a cannula assembly disposed proximate said open second end, said cannula assembly comprising a deformable wall and a cannula extending through said wall, said cannula having a first end disposed proximate said penetrable plug and a second end extending inwardly of said hollow housing, said first end of said cannula being adapted to pierce said penetrable plug upon deformation of said wall.

21. A device as defined in claim 20 in which said liquid component comprises a diluent.

22. A device as defined in claim 20 further including a substrate receivable within said sealed cartridge, said beneficial agent being removably affixed to said substrate.

23. A device as defined in claim 22 in which said beneficial agent comprises a drug.

* * * * *